(12) United States Patent
Tao et al.

(10) Patent No.: US 11,007,350 B2
(45) Date of Patent: *May 18, 2021

(54) GUIDEWIRE FOR CANNULA PLACEMENT

(71) Applicant: Abiomed, Inc., Danvers, MA (US)

(72) Inventors: Zhenghong Tao, Winchester, MA (US); Michael Thomas Finnegan, North Reading, MA (US)

(73) Assignee: ABIOMED, INC., Danvers, MA (US)

( * ) Notice: Subject to any disclaimer, the term of this patent is extended or adjusted under 35 U.S.C. 154(b) by 68 days.

This patent is subject to a terminal disclaimer.

(21) Appl. No.: 16/381,942

(22) Filed: Apr. 11, 2019

(65) Prior Publication Data

US 2019/0232025 A1    Aug. 1, 2019

Related U.S. Application Data

(63) Continuation of application No. 15/790,107, filed on Oct. 23, 2017, now Pat. No. 10,300,249, which is a
(Continued)

(51) Int. Cl.
*A61M 25/09* (2006.01)
*A61M 60/135* (2021.01)
(Continued)

(52) U.S. Cl.
CPC .......... *A61M 25/09* (2013.01); *A61M 60/135* (2021.01); *A61M 60/148* (2021.01);
(Continued)

(58) Field of Classification Search
None
See application file for complete search history.

(56) References Cited

U.S. PATENT DOCUMENTS 5,363,847 A    11/1994   Viera
5,820,571 A    10/1998   Erades et al.
(Continued)

FOREIGN PATENT DOCUMENTS

EP    0916359 A1    5/1999
EP    2337606 A1    6/2011
(Continued)

OTHER PUBLICATIONS

International Search Report for PCT/US2016/052781, dated Oct. 17, 2016.
(Continued)

*Primary Examiner* — Brian T Gedeon
(74) *Attorney, Agent, or Firm* — Botos Churchill IP Law LLP

(57) ABSTRACT

A guidewire for backloading and inserting a percutaneous pump affixed to a cannula includes a proximal section made of a first material, with a first diameter, a rounded proximal end, and a distal end. The guidewire also includes a distal section made of a second material, with a second diameter which is greater than the first diameter, a distal end, and a proximal end abutting the distal end of the proximal section. The first material of the proximal section is selected to be softer than a material of the percutaneous pump to reduce damage to the pump during backloading. The distal section of the guidewire is configured to be stiffer than the proximal section to insert the percutaneous pump in a desired location without damaging the guidewire.

20 Claims, 7 Drawing Sheets

Related U.S. Application Data continuation of application No. 14/862,090, filed on Sep. 22, 2015, now Pat. No. 9,821,146.

(51) Int. Cl.
*A61M 60/148* (2021.01)
*A61M 60/205* (2021.01)

(52) U.S. Cl.
CPC . *A61M 60/205* (2021.01); *A61M 2025/09083* (2013.01); *A61M 2025/09133* (2013.01)

(56) References Cited

U.S. PATENT DOCUMENTS

| | | |
|---|---|---|
| 6,007,478 A | 12/1999 | Siess et al. |
| 7,731,675 B2 | 6/2010 | Aboul-Hosn et al. |
| 8,795,576 B2 | 8/2014 | Tao et al. |
| 8,814,776 B2 | 8/2014 | Hastie et al. |
| 8,992,406 B2 | 3/2015 | Corbett |
| 2004/0167440 A1 | 8/2004 | Sharrow |
| 2004/0254602 A1 | 12/2004 | Lehe et al. |
| 2006/0064036 A1 | 3/2006 | Osborne et al. |
| 2015/0328382 A1 | 11/2015 | Corbett et al. |

FOREIGN PATENT DOCUMENTS

| | | |
|---|---|---|
| WO | 9749448 A1 | 12/1997 |
| WO | 2003103745 A2 | 12/2003 |
| WO | 2010078544 A1 | 7/2010 |
| WO | 2012075262 A1 | 6/2012 |

OTHER PUBLICATIONS

Supplementary EP Search Report for EP 16 84 9462, dated Sep. 7, 2018.

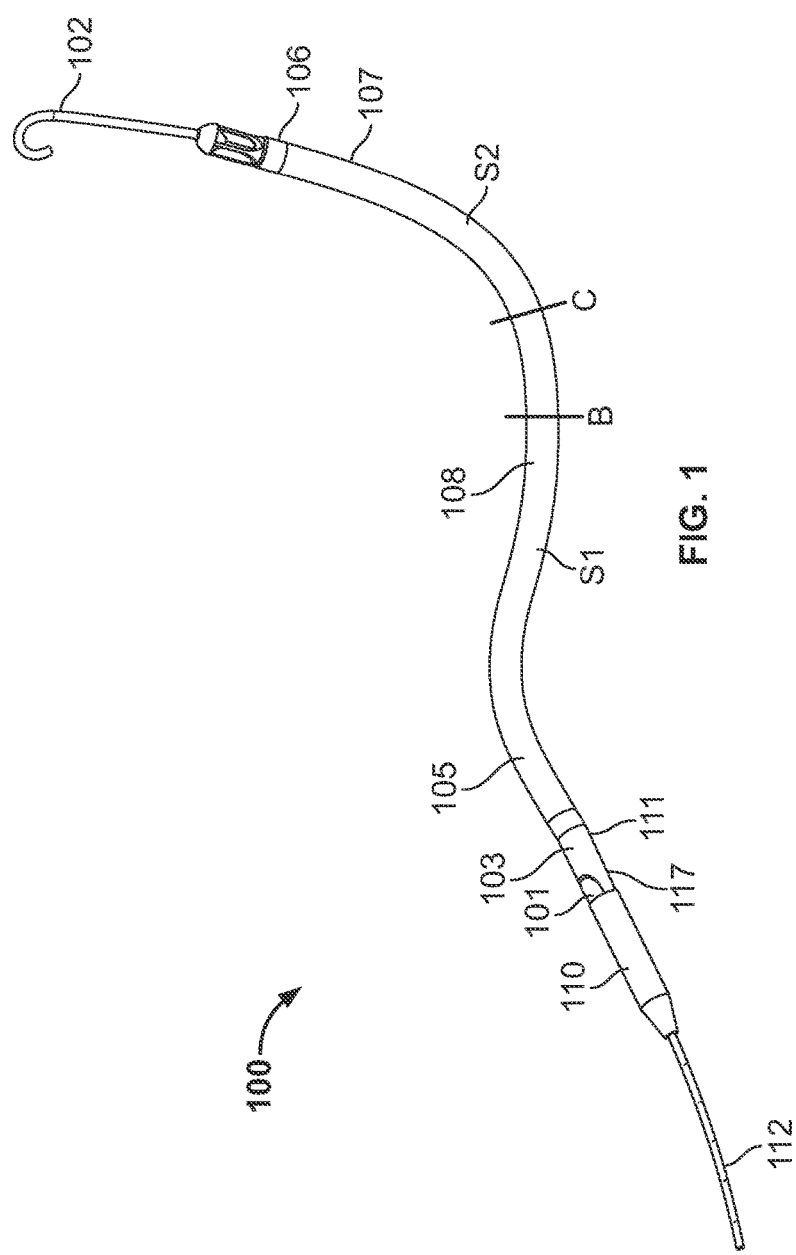
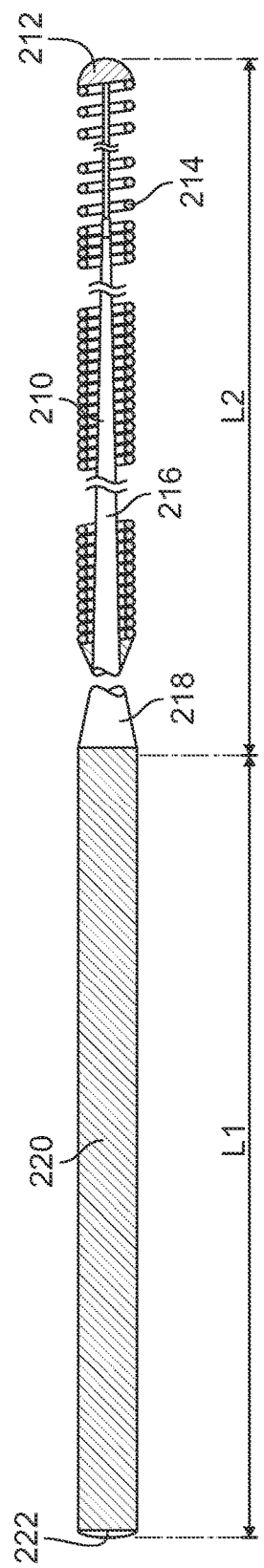
FIG. 1
FIG. 2 (Related Art)

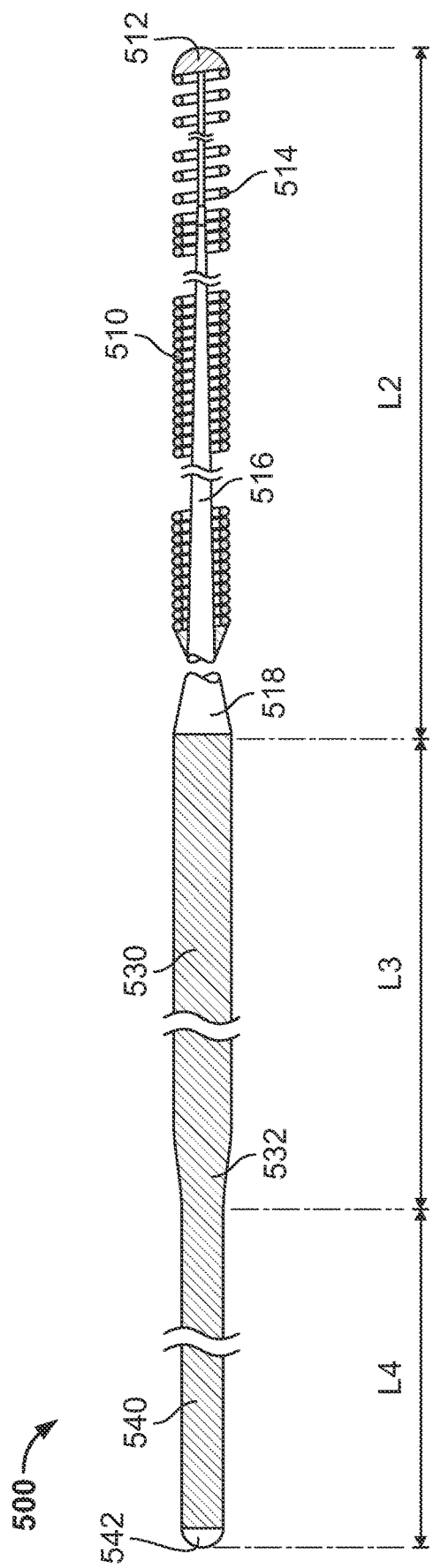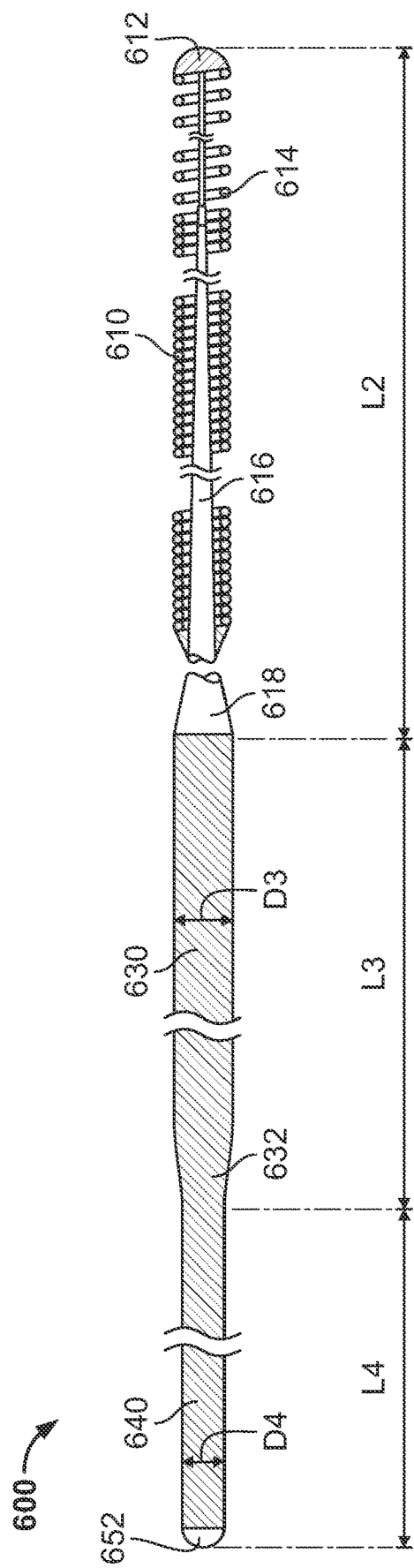
FIG. 5
FIG. 6

FIG. 9

| | Related Art Guidewire | Improved Guidewire (Proximal section) | Improved Guidewire (Distal section) |
|---|---|---|---|
| Diameter | D1 (0.025") | D2 (0.018") | D1 (0.025") |
| Length | L1 | L4 | L3 |
| Function | Steering and Guiding | Steering | Guiding |
| Materials | Stainless steel | Stainless core wire with or without coating, Stainless core wire with coil jacket, Stainless core wire with plastics tubing jacket, Nitinol wire, Plastics string | Stainless core wire with or without coating, Stainless core with coils jacket, Stainless core wire with plastics tube jacket, Nitinol wire |
| Coating | No | Yes | No |

FIG. 10

| | Related Art Proximal Section | Improved Proximal Section |
|---|---|---|
| OD | 0.025" (same as intermediate pump delivery section OD) | 0.018" |
| Backloading force through pump (max) | 1.5N | 0.3N |
| Guidewire sliding force with lumen (max) | N/A | 1.9N (initial resistance) 0.7N (stable sliding force) |

GUIDEWIRE FOR CANNULA PLACEMENT

CROSS-REFERENCE TO RELATED APPLICATIONS

This application relates to U.S. Pat. No. 6,007,478, and is a continuation of U.S. application Ser. No. 15/790,107, filed Oct. 23, 2017 (now U.S. Pat. No. 10,300,249), which is a continuation of U.S. application Ser. No. 14/862,090, filed on Sep. 22, 2015 (now U.S. Pat. No. 9,821,146). The specifications of each of the foregoing applications are hereby incorporated by reference in their entirety.

BACKGROUND

A blood pump, such as a percutaneous intracardiac blood pump assembly, is introduced in the heart to deliver blood from the heart into an artery, such as the pulmonary artery. When deployed in the heart, a blood pump assembly pulls blood from the left ventricle of the heart and expels blood into the aorta, or pulls blood from the right ventricle and expels blood into the pulmonary artery, through a cannula. Blood pump assemblies are introduced surgically or percutaneously during a cardiac procedure through the vascular system. In one common approach, pump assemblies are inserted by a catheterization procedure through the femoral artery using a guidewire.

An introducer is inserted into the femoral artery through an arteriotomy to create an insertion path. A placement guidewire is then advanced distal end first through the sheath into the artery. Once the guidewire has been inserted into the artery, the pump assembly, including a pump and a cannula, is backloaded onto the proximal end of the guidewire and pushed along the guidewire and into the patient. The pump assembly may then be used in conjunction with a catheter.

As defined herein, backloading involves inserting the proximal end of the guidewire, which remains outside the patient, into the distal end of the catheter and then advancing the catheter distally over the wire. Backloading the pump assembly allows the guidewire to remain in position within the patient while different size catheters or sheaths are inserted and removed during the course of a procedure. But the cannula of the pump assembly can have a tortuous shape, or the cannula can be stiff. In these cases, the guidewire may not be stiff enough to allow backloading of the pump through to the pulmonary valve, and as a result the cannula of the pump may displace the guidewire out of the pulmonary valve. For example, for systems delivering blood from the inferior vena cava to an opening in the pulmonary artery, the cannula of the pump may be a 3D shape with two "S" turns in different planes. This can make backloading and insertion of the pump assembly into a patient particularly difficult.

SUMMARY

Systems, methods, and devices for an improved guidewire for cannula placement are presented. The improved guidewire facilitates insertion of the guidewire through a heart pump without damaging the pump. This improved guidewire is particularly helpful for pumps having complex or tortuous geometries, such as the IMPELLA RP pump or any other pump adapted for use in the right ventricle (e.g., between the inferior vena cava and the pulmonary artery).

The improved guidewire disclosed herein can be inserted into the arterial system of a patient through an arteriotomy. The guidewire includes a first distal section, an intermediate pump delivery section, and a backloading proximal section. The first distal section, is inserted first into the arterial system of the patient. The first distal section is flexible and has a rounded end which allows a physician to insert the guidewire with minimal trauma to the patient. For example, during insertion the first distal section of the guidewire may come into contact with the walls of the patient's artery, or with a lumen placed inside the patient's artery. Thus, use of a material with low friction and high flexibility for the first distal section, such as a plastic or polymer, can reduce trauma and discomfort to the patient.

The intermediate pump delivery section, is connected to the first distal section. While the first distal section of the guidewire facilitates insertion in the patient, the intermediate pump delivery section facilitates backloading of a pump assembly onto the guidewire. The pump assembly includes a pump affixed to a cannula. During backloading, the proximal end of the guidewire which remains outside the patient must be inserted into the pump and through the cannula, before the pump and cannula can be pushed along the guidewire until reaching the desired site. Depending on the application, the cannula may take different shapes. For example, in the case of some pumps for the right ventricle (e.g., the IMPELLA RP pump), the pump is located at one end of a cannula with a complex three-dimensional shape, including two "S" bends in different planes. Having an intermediate pump delivery section of the guidewire which is stiffer than the first distal section facilitates backloading of the stiff cannula and minimizes the risk of the stiff cannula displacing the guidewire. The pump delivery section can have a larger diameter than the first distal section and can be made of a stiffer material.

The intermediate section of the guidewire is connected to the backloading proximal section. While the intermediate section, also referred to as intermediate pump delivery section, facilitates guiding the pump assembly into position without displacing the guidewire, the backloading proximal section minimizes damage to the pump during the backloading process. Due to its softness and flexibility relative to the intermediate pump delivery section, the backloading proximal section can be inserted into the pump without damaging the pump. This is particularly helpful because the small size of the pump and the guidewire routinely complicate initiation of the backloading process. Inserting the guidewire into the pump through the small gap between the impeller blades and the housing may require several attempts.

In some implementations, the first distal section, the intermediate pump delivery section, and the backloading proximal section of the guidewire have different stiffnesses due to differences in materials, structures, geometries, or a combination thereof.

The guidewire disclosed herein provides a number of possible advantages. The guidewire is flexible enough at its proximal end to pass through the pump without unnecessary damage. At the same time, the guidewire is stiff enough at its distal end to guide the cannula into place during backloading without being displaced. This can help avoid multiple insertions of the guidewire into the patient and minimizes the risk of damage to the patient's arterial system.

In one aspect, a system for inserting a percutaneous pump includes a percutaneous pump, a cannula and a guidewire. The cannula has a cannula diameter, a proximal inlet, and a distal outlet. The percutaneous pump is located at, and affixed to, the distal outlet of the pump. The guidewire includes a proximal section with a first stiffness and having a first diameter, and a distal section connected to the proximal section, the distal section with a second stiffness and a second diameter which is greater than the first diameter. The distal section is stiffer than the proximal section to insert the cannula and position it in a desired location without displacing the guidewire.

In certain implementations, the proximal section of the guidewire uses a first material which is softer than a material of the percutaneous pump to reduce damage to the percutaneous pump during backloading of the cannula onto the guidewire.

In certain implementations, the proximal section is made of a first material with the first stiffness and the distal section is made of a second material with the second stiffness.

In certain implementations, the proximal section is made of a first structure with the first stiffness and the distal section is made of a second structure with the second stiffness.

In certain implementations, the guidewire includes a distal tip which is connected to a distal end of the distal section.

In certain implementations, the cannula has a three-dimensional shape with a first "S" bend in a first plane, and a second "S" bend in a second plane, where the second plane is different from the first plane.

In certain implementations, the proximal section has a rounded proximal end made of a third material.

In certain implementations, a ratio of a diameter of the proximal section over a diameter of the distal section is 0.72.

In certain implementations, a stiffness of the proximal section is lower an a stiffness of the distal section.

In certain implementations, the proximal section extends over 40 to 75% of a total length of the guidewire.

In another aspect, a guidewire for backloading and inserting a percutaneous pump includes a proximal section and a distal section. The proximal section is made of a first material and has a first diameter. The proximal section includes a rounded proximal end and a distal end. The distal section is made of a second material and has a second diameter. The second diameter of the distal section is greater than the first diameter of the proximal section. A proximal end of the distal section abuts the distal end of the proximal section. The first material of the proximal section is selected to be softer than a material of the percutaneous pump to reduce damage to the pump housing or blades during backloading of the percutaneous pump onto the guidewire. The distal section is configured to be stiffer than the proximal section such that the percutaneous pump can be inserted and moved to a desired location without displacing the guidewire.

In some implementation, a stiffness of the second material is greater than a stiffness of the first material.

In some implementation, the proximal section is made of a first structure and has a first stiffness and the distal section is made of a second structure and has a second stiffness.

In some implementation, the proximal section is made of a first structure and has a first stiffness, and the distal section is made of a second structure and has a second stiffness.

In certain implementations, a stiffness of the proximal section is lower than a stiffness of the distal section.

In certain implementations, the proximal section is coated and the distal section is not coated.

In certain implementations, a ratio of a diameter of the proximal section over a diameter of the distal section is 0.72.

In certain implementations, the proximal end extends over 40 to 75% of a total length of the guidewire.

In certain implementations, the proximal section includes a distal tip which is connected to a distal end of the distal section.

In certain implementations, the rounded proximal end of the proximal section is made of a third material.

In another aspect, a method for inserting a percutaneous pump includes inserting a guidewire into a cannula through a distal end of the cannula which supports the percutaneous pump, and pushing the guidewire through the percutaneous pump and cannula. The guidewire includes a proximal section with a first stiffness and a first diameter, and a distal section connected to the proximal section, the distal section with a second stiffness and a second diameter greater than the first diameter. The distal section is stiffer than the proximal section to insert the cannula in a desired location without displacing the guidewire.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 1 shows an illustrative embodiment of a cannula assembly;

FIG. 2 shows a lateral cross-section of a conventional guidewire;

FIG. 5 shows a lateral cross-section of a first illustrative embodiment of a guidewire;

FIG. 6 shows a lateral cross-section of a second illustrative embodiment of a guidewire;

FIGS. 9 and 10 show tables of data related to properties of the guidewire in FIG. 2 and a guidewire in any of FIGS. 2-8;

DETAILED DESCRIPTION

Figure 3:
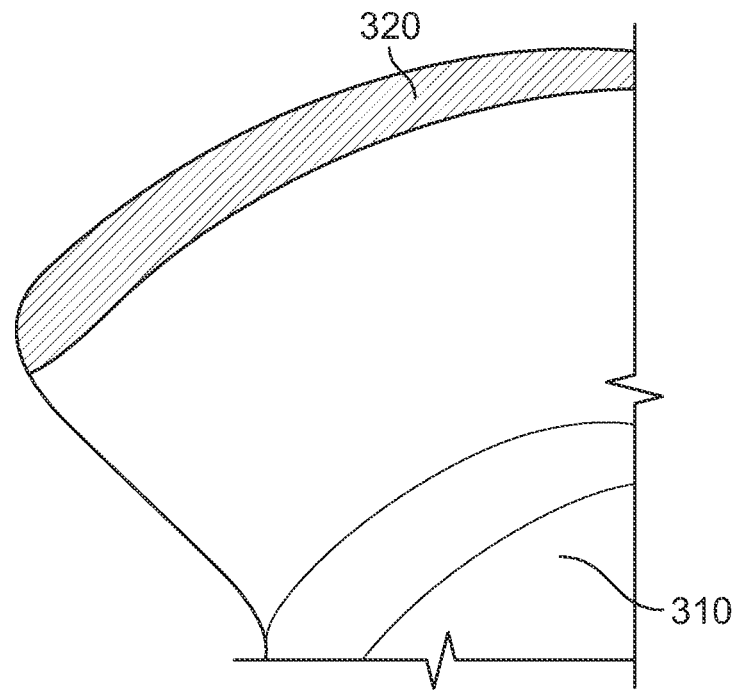
FIGS. 3 and 4 show illustrative damage to blades of a percutaneous pump, resulting from backloading the percutaneous pump on a conventional guidewire.

To provide an overall understanding of the systems, methods, and devices described herein, certain illustrative embodiments will be described. Although the embodiments and features described herein are specifically described for use in connection with a percutaneous blood pump system for the right ventricle, it will be understood that all the components and other features outlined below may be combined with one another in any suitable manner and may be adapted and applied to blood pump systems for the left ventricle or other types of cardiac therapy and cardiac assist devices, including balloon pumps, cardiac assist devices implanted using a surgical incision, and the like.

The systems, methods, and devices described herein provide a guidewire having a first proximal section and a second distal section such that a cannula can be inserted over a guidewire without displacing the guidewire and without damaging a pump coupled to the cannula. The proximal section of the guidewire is less stiff than the distal section of the guidewire due to the geometry or the material of the proximal section. For example, the proximal section of the guidewire may have a diameter which is smaller than a diameter of the distal section. In another example, the proximal section of the guidewire may be made of a material which is less stiff than a material of the distal section of the guidewire. In yet another example, the proximal section of the guidewire may have a structure which is less stiff than a structure of the distal section of the guidewire. The lower stiffness of the proximal section, relative to the stiffness of the distal section, allows physicians to more easily insert the guidewire into a percutaneous pump located at a distal end of a cannula. In particular, physicians may be able to insert the proximal section of the guidewire into the gap located between the housing and the blades of the percutaneous pump without damaging the blades, and without damaging or rupturing the housing.

FIG. 1 shows an illustrative embodiment of a blood pump assembly 100. The blood pump assembly 100 includes a pump 101, a pump housing 103, a proximal end 105, a distal end 107, a cannula 108, an impeller 109, an extension 102, a catheter 112, an inlet area 110, an outlet area 106, and blood exhaust apertures 117. The catheter 112 is connected to the inlet area 110 of the cannula 108. The inlet area 110 is located near the proximal end 105 of the cannula, and the outlet area 106 is located toward the distal end 107 of the cannula 108. The inlet area 110 includes a pump housing 103 with a peripheral wall 111 extending about a rotation axis 113 of the impeller blades 115, positioned radially outward of the inner surface with respect to the rotation axis 113 (not shown) of the impeller 109 (not shown). The impeller 109 is rotatably coupled to the pump 101 at the inlet area 110 adjacent to the blood exhaust apertures 117 formed in the wall 111 of the pump housing 103. The pump housing 103 may be composed of a metal in accordance with implementations. The extension 102, also referred to as a "pigtail," is connected to the distal end 107 of the cannula 108 and assists with stabilizing and positioning the blood pump assembly 100 into the correct position in the heart. The pigtail 102 is configurable from a straight to a partially curved configuration. The pigtail 102 may be composed, at least in part of a flexible material, and may have dual stiffness.

The cannula 108 has a shape which matches the anatomy of the right ventricle of a patient. In this exemplary embodiment, the cannula has a proximal end 105 arranged to be located near the patient's inferior vena cava, and a distal end 107 arranged to be located near the pulmonary artery. The cannula 108 includes a first segment S1 extending from the inflow area to a point B between the inlet area 110 and the outlet area 106. The cannula 108 also includes a second segment S2 extending from a point C, which is between the inlet area 110 and the outlet area 106, to the outlet area 106. In some implementations B and C may be at the same location along cannula 108. The first segment S1 of the cannula forms an 'S' shape in a first plane. In some implementations, segment S1 can have curvatures between 30 degrees and 180 degrees. The second segment S2 of the cannula forms an 'S' shape in a second plane. In some implementations, segment S2 can have curvatures between 30 degrees and 180 degrees (e.g., 40°, 50°, 60°, 70°, 80°, 90°, 100°, 110°, 120°, 130°, 140°, 150°, 160°, or 170°). The second plane can be different from the first plane. In some implementations, the second plane is parallel or identical to the first plane.

In some implementations, the blood pump assembly 100 is inserted percutaneously through the femoral artery and into the right ventricle. Alternatively, in some implementations the blood pump assembly 100 may be inserted percutaneously through the femoral artery and into the left ventricle. When properly positioned, the blood pump assembly 100 delivers blood from the inlet area 110, which sits inside the patient's left ventricle, through the cannula 108, to the blood exhaust apertures 117 of the pump housing 103 positioned in the ascending aorta.

FIG. 2 shows a lateral cross-section of a conventional guidewire 200. The conventional guidewire includes a distal section 210, a distal tip 212, a coil wire 214, a core wire 216, a transition region 218, a proximal section 220, a proximal end 222, and a transition section 218. The coil wire 214 surrounds the core wire 216. The core wire 216 has a diameter which decreases from the transition region 218 to the tip of the distal section 212. The distal section 210 has a length L2, which is between 25-50% of the total length of the core wire 216. The core wire 216 also includes a proximal section 220, extending between a proximal end 4222 and the transition section 218. The proximal section 220 has a constant diameter. The proximal section has a length between 75-50% of the total length of the core wire 216. The distal section 210 of the core wire is more flexible than the proximal section of the guidewire 200. This allows a physician initially placing the guidewire into a patient to minimize damage to the arterial system of the patient.

Figure 4:
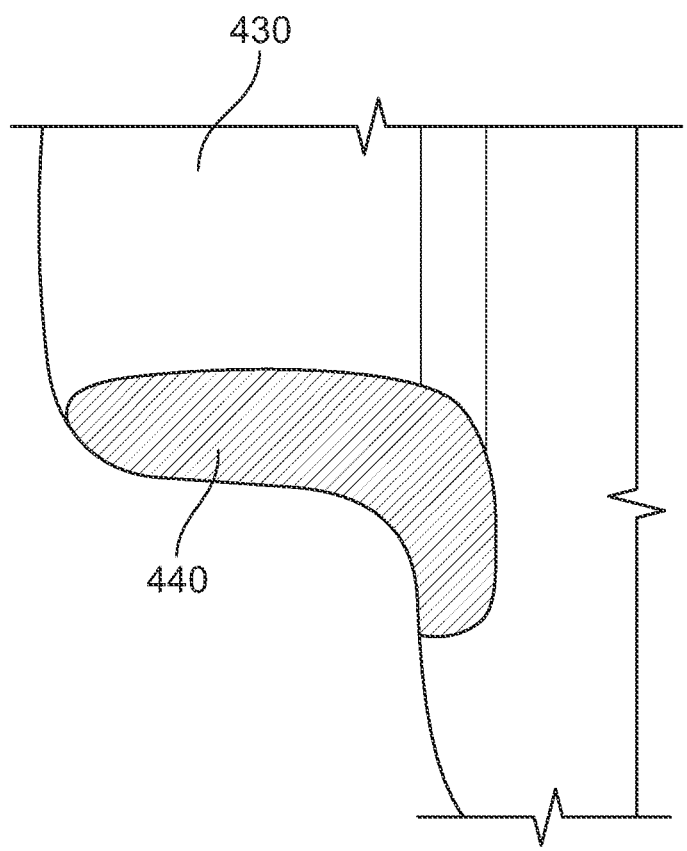

FIGS. 3 and 4 show illustrative damage to a blade of a percutaneous pump. Exemplary blades 310 and 430 include portions 320 and 440 which were scratched or dented or both by attempting to insert a conventional guidewire between the pump housing (e.g., pump housing 103 in FIG. 1) and the blades (e.g., impeller blades 115 in FIG. 1). In this example, contact between the guidewire and a pump element results in the pump element being scratched or indented (as shown in FIGS. 2 and 3) rather than in the guidewire being scratched or indented. Although only scratches and indentations are shown, in some cases the pump housing can be punctured when inserting a conventional guidewire. This is particularly a concern when using a guidewire made of a material with a higher scratch hardness, indentation hardness or rebound hardness than a material used for the pump elements.

As discussed above, when a guidewire (e.g., guidewire 200 in FIG. 2) is not stiff enough, backloading and insertion of a pump assembly (e.g., pump assembly 100 in FIG. 1) into a patient may be particularly difficult. Accordingly, some physicians may use a stiffer guidewire to backload a pump (e.g., pump 101 in FIG. 1) without displacing the guidewire 200 out of the pulmonary valve. However, for particular pumps, such as the IMPELLA RP pump which is used in combination with an "S" turn cannula (e.g., cannula 108 in FIG. 1), a stiffer guidewire may not be a viable solution. In the exemplary embodiment of the IMPELLA RP pump (e.g., pump 101 in FIG. 1), the pump is so small that the passage between the pump housing (e.g., pump housing 103 in FIG. 1) and the blades of the pump (e.g., impeller blades 115 in FIG. 1) is on the order of millimeters.

Furthermore, due to their size and complexity the components of the IMPELLA RP pump such as the housing (e.g., housing 103 in FIG. 1) and the blades (e.g., impeller blades 115 in FIG. 1) are particularly expensive to manufacture or replace. Any undesired contact between the guidewire and the pump elements, instead of having the guidewire pass straight through the aforementioned gap, can result in damage. This is particularly true for a stiff guidewire, such as a guidewire made of a material with a higher scratch hardness, indentation hardness or rebound hardness than a material used for the pump elements. A guidewire with increased stiffness throughout, either via an increased diameter or via material properties, could damage the housing or blades of the pump even more than a conventional guidewire.

FIG. 5 shows a lateral cross-section of a first illustrative embodiment of a guidewire 500. The guidewire 500 includes a soft distal section 510, a distal tip 512, a coil wire 514, a core wire 516, a transition area 518, an intermediate pump delivery section 530, a transition area 532, a backloading proximal section 540, and a proximal tip 542. The soft distal section 510 extends between the transition area 518 and the distal tip 512. In use, the soft distal section 510 is inserted first into the patient. The soft distal section 510 includes the core wire 516 and the coil wire 518 coiled around the core wire 516. The core wire 516 has a diameter which decreases from the transition region 518 to the distal tip 512. Instead of a single proximal section as in the guidewire 200, the guidewire 500 includes two sections, the intermediate pump delivery section 530 and the backloading proximal section 540. The intermediate pump delivery section 530 and the backloading proximal section 540 are coupled to the intermediate pump delivery section 530 by a transition area 532. The intermediate pump delivery section 530 extends between the transition area 532 and the transition area 518. The intermediate pump delivery section 530 is the portion of the guidewire 500 with the widest diameter. The intermediate pump delivery section 530 may have a constant diameter. In some implementations, the intermediate pump delivery section 530 is not the widest section of the guidewire.

The backloading proximal section 540 extends between the proximal tip 542 and the transition section 532. The backloading proximal section 540 has a constant diameter. In some implementations, the diameter of the proximal section 540 varies. The material and the structure of the backloading proximal section 540 and the intermediate pump delivery section 530 may be similar or the same. The backloading proximal section 540 is more flexible than the intermediate pump delivery section 530 because the backloading proximal section 540 has a diameter which is smaller than the diameter of the intermediate pump delivery section 530. The smaller diameter of the backloading proximal section facilitates the introduction of the guidewire through the pump with low forces. In some implementations, the backloading proximal section 540 is more flexible than the intermediate pump delivery section 530 because the backloading proximal section 540 is formed of a material or a structure which is less stiff than the material or structure of the intermediate pump delivery section 530.

In certain implementations, the backloading proximal section 540 is more flexible than the intermediate pump delivery section 530 by having a material composition which is 100% a material which is more flexible than a material of the intermediate pump delivery section 530. The intermediate pump delivery section 530 can have a material composition which is 100% a material stiffer than the material of the backloading proximal section 540. The stiffer material of the intermediate pump delivery section 530 may consist of any number of materials including but not limited to polyurethane or resin impregnated fibers. The more flexible material may consist of any number of materials including but not limited to a silicone compound. In some implementations, the two different materials may have the same chemical composition, but different degrees of polymerization, crystallinity, or any other property.

The material of the backloading proximal section 540 may be selected to reduce damage to the pump elements when there is undesired contact between the guidewire and any of the pump elements. In particular, the material of the backloading proximal section can be selected to have a lower scratch hardness, indentation hardness or rebound hardness than a material used for the pump elements.

The proximal tip 542 of the backloading proximal section 540 is rounded and is made with or coated with a material different from the remainder of the backloading proximal section 540. For example a lubricating coating or lubricated material can be used for the proximal tip 542. This allows a physician to insert the proximal tip 542 and the backloading proximal section 540 of the guidewire more easily into the pump and the cannula. In turn, these features can help reduce damage to the blades and housing of the percutaneous pump into which the guidewire is inserted. The proximal tip 542 can be attached to the backloading proximal section 540 by adhesive or solvent bonding, mechanical fastening, insert molding, or any other suitable joining mechanism or combinations thereof. Alternatively, the proximal tip 542 can be integral to the backloading proximal section.

FIG. 6 shows a lateral cross-section of a second illustrative guidewire 600 according to certain embodiments. The guidewire 600 includes a soft distal section 610, a distal tip 612, a coil wire 614, a core wire 616, a transition area 618, an intermediate pump delivery section 630, a transition area 632, a backloading proximal section 640, and a proximal tip 642. The guidewire 600 includes a distal section 610 which extends between the transition area 618 and the distal tip 612 and which is inserted first into the patient. The soft distal section 610 includes a core wire 616 with a diameter which decreases from the transition region 638 to the distal tip 612. The soft distal section 610 also includes a coil wire 614 which is coiled around the core wire 616. The soft distal section 610 extends over a length L2, which can be 25-50% (e.g., 30%, 35%, 40%, 45%) of the total length of the guidewire 600. Preferably, the length L2 is between 25-35% of the total length of the guidewire 600. Even more preferably, the length L2 is 30% of the total length of the guidewire 600. The guidewire 600 further comprises, instead of the proximal section 220 for example, two sections, the intermediate pump delivery section 630, and the backloading, proximal section 640 coupled to the intermediate pump delivery section 630 by a transition area 632. The intermediate pump delivery section 630 extends between the transition area 632 and the transition area 618. The intermediate pump delivery section 630 can have a constant diameter D3, which may be between 0.02 and 0.03," with a preferred value of 0.025". The intermediate pump delivery section 630 has a length L3 which is between 30% and 60% (e.g., 35%, 40%, 45%, 50%, 55%) of the length of the guidewire. In particular, D3 can be larger than any diameter of the backloading proximal section 640. The backloading proximal section 640 has a constant diameter D4, which may be between 0.017" and 0.019" with a preferred value of 0.018". The backloading proximal section 640 can have a length L4 which is 40-75% (e.g., 45%, 50%, 55%, 60%, 65%, 75%) of the length of the guidewire. For example, for a guidewire with a total length of 260 mm, the backloading proxima section 640 has a length of at least 100 mm.

At least one advantage of the diameter D4 of the backloading proximal section 640 being smaller than the diameter D3 of the intermediate pump delivery section 630 is increased flexibility of the backloading proximal section 640. Another advantage is a reduction in the overall weight of the guidewire. This reduction in weight is achieved because the backloading proximal section 640 is made lighter, and that backloading proximal section accounts for a substantial portion of the overall length of the guidewire 600 (e.g., 10%, 20%, 30%, 40%, 50%, 60%, 70%, 80%, 90%, or more). A lighter guidewire is easier for physicians to insert into a patient and may also cause less damage when inserted into a pump, such as the pump 101 of the blood pump assembly 100.

The backloading proximal section 640 may end with the proximal tip 652. The proximal tip 642 may be rounded and may be made with or coated with a different material than a material of the backloading proximal section 640. For example a lubricating coating or lubricated material can be used for the proximal tip 652. This allows a physician to insert the proximal tip and the backloading proximal section of the guidewire more easily into the pump and the cannula. In turn, these features can help reduce damage to the blades and housing of the percutaneous pump the guidewire is being inserted into.

Figure 7:
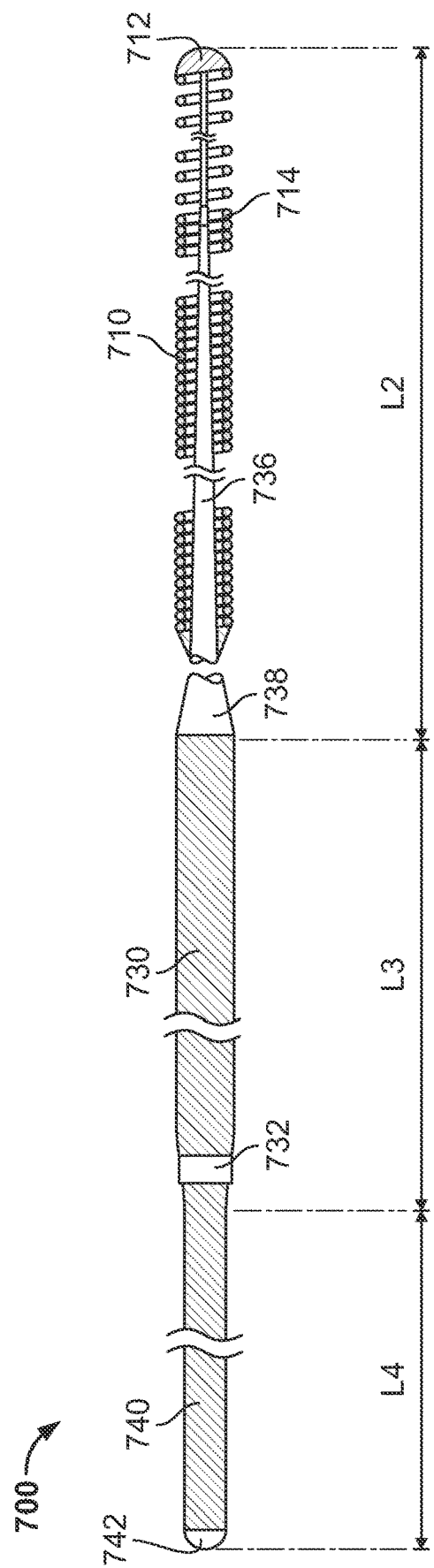
FIG. 7 shows a lateral cross-section of a third illustrative embodiment of a guidewire.

FIG. 7 shows a lateral cross-section of a third illustrative guidewire 700 according to certain embodiments. The guidewire 700 includes a soft distal section 710, a distal tip 712, a coil wire 714, a core wire 716, a transition area 718, an intermediate pump delivery section 730, a transition area 732, a backloading proximal section 740, and a proximal tip 742. The guidewire distal section 710 extends between the transition area 718 and the distal tip 712, and is inserted first into the patient. The soft distal section 710 can include a core wire 716 with a diameter which decreases from the transition region to the distal tip 712. The soft distal section 710 includes the coil wire 714 which is coiled around the core wire 716. The guidewire 700 further comprises, instead of the proximal section 220 for example, two sections, an intermediate pump delivery section 730 and a backloading proximal section 740. The backloading proximal section 740 is coupled to the intermediate pump delivery section 730 by a transition area 732. A material of the backloading proximal section 740 is different than a material of the intermediate pump delivery section 730. The transition area 732 can be a conical section with a first diameter equal to the diameter of the backloading proximal section 740 and a second diameter equal to the diameter of the intermediate pump delivery section. Alternatively, the transition 732 may be a weld. The transition 732 may be an abrupt transition resulting from joining two sections of different flexibilities in a butt joint or a stepped joint. Alternatively, the transition 732 can be gradual by employing a composite construction such that the content of a more flexible material (e.g., the main material of the backloading proximal section 740) gradually displaces a stiffer material (e.g., the main material of the intermediate pump delivery section 730). The use of different materials for the backloading proximal section 740 and the intermediate pump delivery section 730 allows one section to be optimized for insertion (e.g., the backloading proximal section 740) and another to be optimized for pump delivery (e.g., the intermediate pump delivery section 730). This may also reduce the guidewire's weight, cost, or both.

Figure 8:
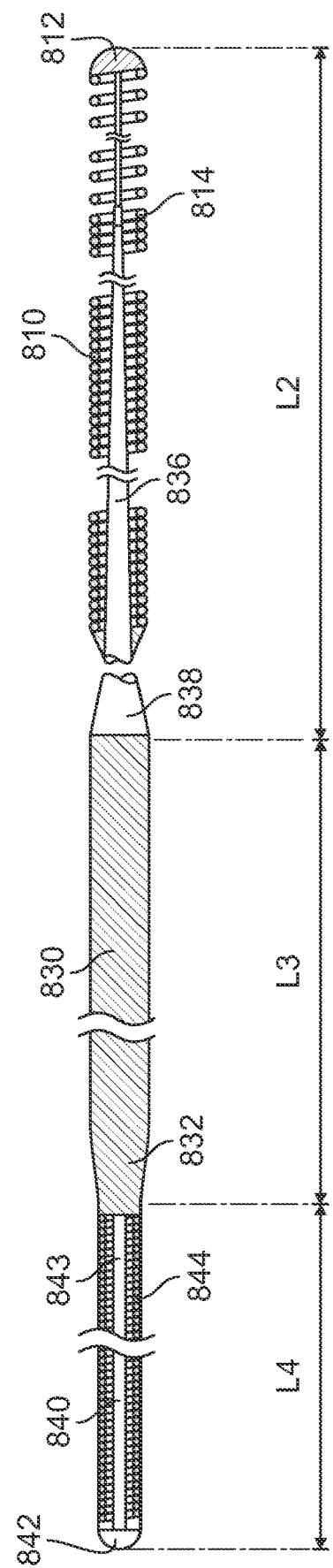
FIG. 8 shows a lateral cross-section of a fourth illustrative embodiment of a guidewire.

FIG. 8 shows a lateral cross-section of a fourth illustrative guidewire 800 according to certain embodiments. The guidewire 800 includes a soft distal section 810, a distal tip 812, a coil wire 814, a core wire 816, a transition area 818, an intermediate pump delivery section 830, a transition area 832, a backloading proximal section 840, and a proximal tip 842. The guidewire distal section 810, which is inserted first into the patient, extends between the transition area 818 and the distal tip 812. The soft distal section 810 can include a core wire 816 with a diameter which decreases from the transition region 838 to the distal tip 812. The soft distal section 810 can also include a coil wire 814 which is coiled around the core wire 816. The guidewire 800 further comprises, instead of the proximal section 220 for example, two sections, an intermediate pump delivery section 830, and a backloading proximal section 840 coupled to the intermediate pump delivery section 830 by a transition area 832. The intermediate pump delivery section 830 can have a first structure which is a core wire with a constant diameter. The backloading proximal section 840 can have a second structure which includes a core wire 843, and a coil wire 844. The core wire 816 can have a constant diameter. Alternatively, the core wire 843 can be tapered to have a first larger diameter adjacent to the transition area 832, and a second smaller diameter adjacent to the proximal tip 842. The coil wire 844 may be wrapped around the core wire 843. Similar to the core wire 843, the coil wire 844 may have a constant diameter, or may have a diameter which decreases from transition area 832 to proximal tip 842.

The coil wire 844 can impart resistance to radial deformation and can allow the guidewire 800 to regain its original shape even after deformations that it may be subjected to during placement or manipulation in the heart. The coil wire 844 may have any number of cross-sectional shapes including but not limited to round or rectangular cross-sections. The coil wire 844 may also have varying axial density that varies the elasticity or flexibility of the backloading proximal section 840.

FIGS. 9 and 10 are tables summarizing the dimensions and material properties of exemplary embodiments of the guidewire shown in FIGS. 2 and 5-8.

FIG. 9 shows a table indicating diameter, length, function, materials and coating for a related art guidewire (e.g. guidewire 200 in FIG. 2) and an improved guidewire with a proximal section and a distal section (e.g. guidewire in any of FIGS. 5-8). FIG. 9 indicates that the outer diameter D1 of a related art guidewire is 0.025" which is the same as the outer diameter D1 of the improved guidewire distal section. FIG. 9 indicates that the diameter of the improved guidewire proximal section D2 is 0.018.' The function of the related art guidewire is both steering and guiding, whereas the improved guidewire proximal section is used for steering and the improved guidewire distal section is used for guiding. FIG. 9 includes an exemplary list of materials for both the related art guidewire and the improved guidewire (proximal section and distal section). For example, the related art guidewire is generally made of stainless steel. The improved guidewire proximal section may be made of a stainless core wire with a coating, coil jacket or plastics tubing jacket. Alternatively, the proximal section may be made of a Nitinol wire or plastics string. The proximal section of the improved guidewire may be coated. Similarly, the distal section of an improved guidewire may be made of a stainless core wire with a coating, coils jacket or plastics tube jacket. Alternatively, the improved guidewire distal section may be made of Nitinol wire.

FIG. 10 shows force metrics for a related art guidewire proximal section (e.g. 220 in FIG. 2) with an outer diameter of 0.025" and for an improved guidewire proximal section with an outer diameter of 0.018." The maximum backloading force through the pump when using the related art guidewire is 1.5 Newtons. This maximum backloading force is significantly reduced to 0.3 N with the improved proximal guidewire. Furthermore, with the improved guidewire, a maximum sliding force for the guidewire is reduced from 1.9 N of initial resistance to a 0.7 N stable sliding force.

Figure 11:
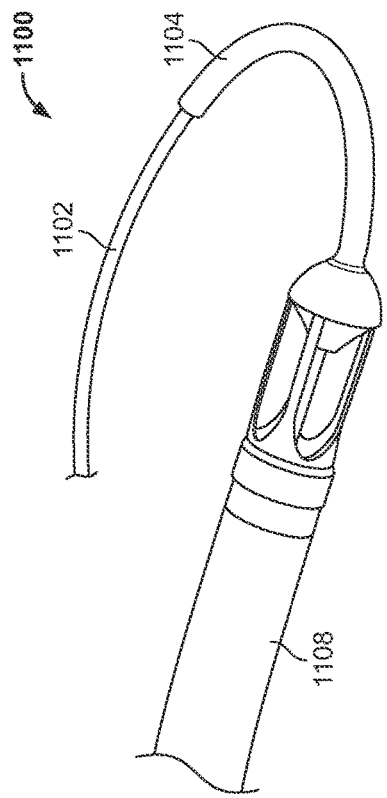
FIG. 11 shows a percutaneous pump being backloaded on a guidewire according to one of the illustrative embodiments of FIGS. 5-8.

FIG. 11 shows a system 1100, with a percutaneous pump already backloaded on a guidewire according to one of the illustrative embodiments of FIGS. 5-8. The system 1100 includes a guidewire 1102, a pigtail 1104 and a cannula 1108. In the example of FIG. 11, the system 1100 is curved to follow the shape of the pulmonary valve (not shown). As a physician backloads the pump and cannula 1108 onto the guidewire 1102, the guidewire 1102 passes through the pigtail 1104, through the cannula 1108, and in the gap located between the blades and the housing of the pump.

Figure 12:
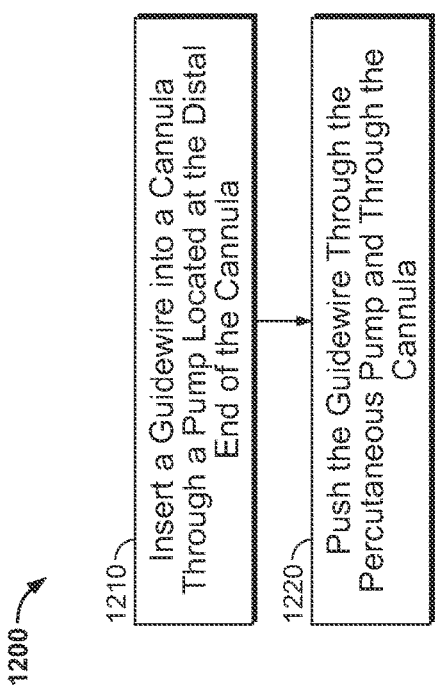
FIG. 12 shows an illustrative process for inserting a guidewire.

FIG. 12 shows a method 1200 for inserting a percutaneous pump according to certain implementations. The method 1200 may be implemented to insert a percutaneous pump, e.g., pump 101, onto a guidewire including but not limited to the guidewires described in any of the aforementioned implementations. The method 1200 may be implemented by inserting a guidewire, previously positioned into the artery of a patient, into a cannula through a distal end of the cannula (step 1210), the distal end of the cannula supporting the percutaneous pump. The method 1200 further includes pushing the guidewire through the percutaneous pump (step 1220). The guidewire pushed through the percutaneous pump includes a proximal section with a first stiffness and a first diameter, and a distal section connected to the proximal section, the distal section with a second stiffness and a second diameter greater than the first diameter. The distal section of the guidewire is stiffer than the proximal section to insert the cannula in a desired location without displacing the guidewire.

At least one benefit of the method 1200 is that it reduces the number of insertions of the guidewire into the patient, and minimizes the risk of damage to the patient's arterial system. The method 1200 uses backloading of the guidewire to reduce the number of insertions into the patient. Another benefit of the method 1200 is that it facilitates insertion of the guidewire into a pump, such as the pump 101 of the blood pump assembly 100. This reduces the risk of damage during insertion.

In alternative embodiments, the percutaneous pump may be backloaded on the guidewire prior to the guidewire being positioned inside the artery of the patient. In alternative embodiments, the percutaneous pump may be backloaded on the guidewire before the percutaneous pump is coupled to the cannula.

Variations and modifications will occur to those of skill in the art after reviewing this disclosure. For example, in some implementations, any of the alternative embodiments described in FIGS. 5-8 may be combined. For example, the coil structure of the proximal end of the guidewire in FIG. 7 may be combined with the different guidewire materials described with respect to FIGS. 5-6. In another example, the coil structure of the proximal end of the guidewire in FIG. 7 may be combined with a weld transition described in relation to FIG. 6. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

It is important to note that the constructions and arrangements of apparatuses or the components thereof as shown in the various exemplary implementations are illustrative only. Although only a few implementations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative implementations. Other substitutions, modifications, changes and omissions may also be made in the design, operating conditions and arrangement of the various exemplary implementations without departing from the scope of the present disclosure.

While various inventive implementations have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive implementations described herein. More generally, those skilled in the art will readily appreciate that, unless otherwise noted, any parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive implementations described herein. It is, therefore, to be understood that the foregoing implementations are presented by way of example only and that, within the scope of the appended claims and equivalents thereto, inventive implementations may be practiced otherwise than as specifically described and claimed. Inventive implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

For the purpose of this disclosure, the termed "coupled" means the joining of two members directly or indirectly to one another. Such joining may be stationary or moveable in nature. Such joining may be achieved with the two members or the two members and any additional intermediate members being integrally formed as a single unitary body with one another or within the two members of the two members and any additional intermediate members being attached to one another. Such joining may be permanent in nature or may be removable or releasable in nature.

The indefinite articles "a" and "an," as used herein in the specification and in the claims, unless clearly indicated to the contrary, should be understood to mean "at least one." As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to.

The claims should not be read as limited to the described order or elements unless stated to that effect. It should be understood that various changes in form and detail may be made by one of ordinary skill in the art without departing from the spirit and scope of the appended claims. All implementations that come within the spirit and scope of the following claims and equivalents thereto are claimed.

Examples of changes, substitutions, and alterations are ascertainable by one skilled in the art and could be made without departing from the scope of the information disclosed herein. All references cited herein are incorporated by reference in their entirety and made part of this application.

We claim:

1. A system for percutaneous insertion of a blood pump assembly into a vascular system, the system comprising a guidewire for backloading the blood pump assembly, the guidewire comprising:
   a proximal section with a first stiffness; and
   a distal section with a second stiffness greater than the first stiffness;
   the blood pump assembly comprising one or more blades, wherein a third stiffness of the one or more blades of the blood pump assembly is greater than the first stiffness of the guidewire.

2. The system of claim 1, wherein the proximal section of the guidewire includes a proximal end and a distal end, the distal section includes a proximal end and a distal end, and the proximal end of the distal section is connected to the distal end of the proximal section.

3. The system of claim 2 wherein the guidewire further comprising a soft distal tip at the distal end of the distal section.

4. The system of claim 1, wherein the third stiffness of the one or more blades of the blood pump assembly is greater than the first stiffness so as to reduce damage to the blades when the proximal section of the guidewire is inserted into the blood pump assembly.

5. The system of claim 1, wherein the proximal section and the distal section of the guidewire have different diameters that cause the second stiffness to be greater than the first stiffness.

6. The system of claim 5, wherein a ratio of a diameter of the proximal section of the guidewire to the diameter of the distal section is 0.72.

7. The system of claim 1, wherein the proximal section and the distal section of the guidewire have different materials that cause the second stiffness to be greater than the first stiffness.

8. The system of claim 7, wherein the proximal section of the guidewire comprises at least one of a stainless core wire, a stainless core wire with a coil jacket, a stainless core wire with a plastics tubing jacket, a Nitinol wire, and a plastics string.

9. The system of claim 8, wherein the distal section of the guidewire comprises at least one of a stainless core wire, a stainless core wire with a coil jacket, a stainless core wire with a plastics tubing jacket, and a Nitinol wire.

10. The system of claim 9, wherein a diameter of the stainless core wire is constant.

11. The system of claim 10, wherein a diameter of the stainless core wire increases distally.

12. The system of claim 1, wherein the guidewire further comprising an intermediate section between the distal section and the proximal section.

13. The system of claim 12, wherein the intermediate section of the guidewire has a fourth stiffness, the fourth stiffness being greater than the second stiffness.

14. The system of claim 13, wherein the proximal section, the intermediate section, and the distal section of the guidewire have differences in diameter that cause the second stiffness to be greater than the first stiffness and the fourth stiffness to be greater than the second stiffness.

15. The system of claim 13, wherein the proximal section, the intermediate section, and the distal section of the guidewire have different materials that cause the second stiffness to be greater than the first stiffness, and the fourth stiffness to be greater than the second stiffness.

16. A method for loading, over a guidewire, a pump configured for insertion into a vascular system, the method comprising:
   inserting a guidewire into a cannula through a distal end of the cannula, the distal end of the cannula supporting the pump wherein the pump comprises one or more blades; and
   pushing the guidewire through the pump,
   wherein the guidewire includes a proximal section made with a first stiffness and a distal section with a second stiffness greater than the first stiffness, wherein a third stiffness of the one or more blades of the pump is greater than the first stiffness.

17. The method of claim 16, wherein the inserting the guidewire into the cannula comprises inserting the proximal section of the guidewire proximally into the distal end of the cannula.

18. The method of claim 16, further comprising inserting the guidewire through empty space between the one or more blades of the pump.

19. The method of claim 16, further comprising inserting the pump into the vascular system of a patient.

20. The method of claim 19, further comprising removing the guidewire from the vascular system of the patient.

* * * * *